United States Patent
Barten

(10) Patent No.: US 8,921,644 B2
(45) Date of Patent: Dec. 30, 2014

(54) BRASSICA PLANTS WITH HIGH LEVELS OF ANTICARCINOGENIC GLUCOSINOLATES

(75) Inventor: Piet Barten, Noord-Scharwoude (NL)

(73) Assignee: Beio Zaden B.V., CZ Warmenhuizen (NL)

(*) Notice: Subject to any disclaimer, the term of this patent is extended or adjusted under 35 U.S.C. 154(b) by 2557 days.

(21) Appl. No.: 10/553,301

(22) PCT Filed: Apr. 13, 2004

(86) PCT No.: PCT/NL2004/000244
§ 371 (c)(1),
(2), (4) Date: Aug. 1, 2006

(87) PCT Pub. No.: WO2004/089065
PCT Pub. Date: Oct. 21, 2004

(65) Prior Publication Data
US 2007/0033675 A1    Feb. 8, 2007

(30) Foreign Application Priority Data
Apr. 14, 2003 (NL) ...................................... 1023179

(51) Int. Cl.
A01H 1/00    (2006.01)
A01H 5/00    (2006.01)
A01H 1/04    (2006.01)

(52) U.S. Cl.
CPC ........................................ A01H 1/04 (2013.01)
USPC ......................................... 800/260; 800/306

(58) Field of Classification Search
None
See application file for complete search history.

(56) References Cited

U.S. PATENT DOCUMENTS 6,340,784 B1 * 1/2002 Mithen et al. .................. 800/306

FOREIGN PATENT DOCUMENTS

| WO | WO 97/09889 A | 3/1997 |
| WO | WO 99/27120 A | 6/1999 |
| WO | WO 99/52345 A | 10/1999 |
| WO | WO 03/004619 A | 1/2003 |

OTHER PUBLICATIONS

Hansen, M., Moller, P. and Sorensen, H.; Glucosinolates in Broccoli Stored Under Controlled Atmosphere; J. Amer. Soc. Hort. Sci.; Jun. 1995; pp. 1069-1074; vol. 120, No. 6; American Society for Horticultural Science; Alexandria, VA, United States.
Kushad, M., Brown, A., Kurilich, A., Juvik, J., Klein, B., Wallig, M., Jeffery, E.; Variation of Glucosinolates in Vegetable Crops of Brassica oleracea; J. Agric. Food Chem; 1999; pp. 1541-1548; vol. 47; American Chemical Society; Washington, DC, United States.
Branca Ferdinando et al., "Survey of aliphatic glucosinolates in Sicilian wild and cultivated Brassicaceae", Apr. 2002, Phytochemistry (Oxford), vol. 59, NR. 7, pp. 717-724.
Giamoustaris et al., "Genetics of aliphatic glucosinolates. IV. Side-chain modification in Brassica oleracea" Theoretical and Applied Genetics, Springer, Berlin, DE, vol. 93, 1996, pp. 1006-1010.
Troyer J K et al., "Analysis of glucosinolates from broccoli and other cruciferous vegetables by hydrophilic interaction liquid chromatography" Journal of Chromatography, Elsevier Science Publishers B.V. Amsterdam, NL, vol. 919, No. 2, Jun. 15, 2001, pp. 299-304.
Mithen et al., "Glucosinolates of wild and cultivated Brassica species" Phytochemistry, Pergamon Press, GB, vol. 26, No. 7, 1987, pp. 1969-1973.
Faulkner, K., et al. (1998) "Selective increase of the potential anticarcinogen 4-methylsulphinylbutyl gucosinolate in broccoli", Carcinogenesis, 19(4):605-609.

* cited by examiner

Primary Examiner — Elizabeth McElwain
(74) Attorney, Agent, or Firm — Harness, Dickey & Pierce, P.L.C.

(57) ABSTRACT

A method is for providing plants belonging to the Brassicaceae family with elevated levels of anticarcinogenic glucosinolates. The plants are obtained by 1) the production of a Brassica oleracea plant with elevated levels of anticarcinogenic glucosinolates in the edible parts and 2) the use of the Brassica oleracea plant produced under 1) as a starting material for breeding Brassica varieties with elevated levels of anticarcinogenic glucosinolates.

8 Claims, No Drawings

BRASSICA PLANTS WITH HIGH LEVELS OF ANTICARCINOGENIC GLUCOSINOLATES

The present invention relates to a method for producing plants belonging to the Brassicaceae family with elevated levels of anticarcinogenic glucosinolates. The invention further relates to *Brassica* plants that can be obtained using the method according to the present invention as well as their seeds and parts of plants. The invention further relates to the use of *Brassica* plants for preparing food products and/or pharmaceutical compositions that can be used for prophylaxis and/or treatment of cancer.

The Brassicaceae family includes a large number of important horticultural plants such as cauliflower or romanesco (*Brassica oleracea* convar. *botrytis* var. *botrytis*); broccoli (*Brassica oleracea* convar. *botrytis* var. *cymosa*); broccoli sprout (*Brassica oleracea* convar. *botrytis* var. *asparagoides*); Brussels sprouts (*Brassica oleracea* convar. *oleracea* var. *gemmifera*); white cabbage or oxheart cabbage (*Brassica oleracea* convar. *capitata* var. *alba*); red cabbage (*Brassica oleracea* convar. *capitata* var. *rubra*); Savoy cabbage (*Brassica oleracea* convar. *capitata* var. *sabauda*); kohlrabi (*Brassica oleracea* convar. *acephala* var. *gongyloides*); kale (*Brassica oleracea* convar. *acephala* var. *sabellica*); and Portuguese cabbage (*Brassica oleracea* var. *tronchuda* syn. *costata*).

The Brassicaceae family is characterised by the presence of typical secondary metabolites that influence the odour, the flavour, the nutritional value and the resistance to pathogens. Numbered amongst these metabolites are the water soluble chemical compounds that are designated by the general term glucosinolates. Glucosinolates can be grouped into aliphatic glucosinolates (derived from the amino acid methionine), indolyl glucosinolates (derived from isoleucine or threonine) and the aromatic glucosinolates (derived from phenylalanine).

The basic chemical structure of glucosinolates is depicted by the following chemical formula:

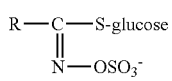

Formula 1: basic chemical structure of glucosinolates wherein R is methionine, isoleucine, threonine or phenylalanine, which may be modified or elongated.

The route for synthesis of glucosinolates in plants has been revealed. The elongase enzyme, which is encoded by the gene BoGSL-ELONG, plays an important role in the synthesis of glucosinolates. This enzyme catalyzes the stepped chain elongation of the glucosinolates. An example of the in vivo synthesis of aliphatic glucosinolates is described in figure 1.

Figure 1 shows that the amino acid methionine is converted to homo-methionine. Various routes for synthesis are possible where the homo-methionione compound is taken as a starting point. Direct aldoxime formation, for example, leads to glucosinolates with a side chain of 3 carbon atoms. If elongase catalyzes one or two extra elongations of the methionine prior to the aldoxime reaction, glucosinolates with side chains of 4 or 5 carbon atoms, respectively, are produced. The enzymes involved in the synthesis of the glucosinolates are depicted in figure 1 as numbers which are specified below the figure.

By proceeding to use different amino acids in combination with various chain elongations and side chain modifying steps, it is possible to produce a large number of different glucosinolates, such as: glucoiberin (3-methylsulphinylpropyl glucosinolate (3MSPG)), progoitrin, sinigrin, glucoraphanin (4-methylsulphinylbutyl glucosinolate (4MSBG)), progoitrin, 4-hydroxybrassicin, glucobrassicin, 4-methoxyglucobrassicin and neoglucobrassicin.

When the plants of the Brassicaceae family are digested by humans and animals, the glucosinolates are broken down hydrolytically in the gastro-intestinal tract by the myrosinase enzyme (which is secreted by the intestinal flora) into a multiplicity of compounds, such as nitriles, isothiocyanates, indoles, amines and thiocyanates, which are then absorbed by the body.

It is known that a number of these breakdown products, in particular the indoles, the isothiocyanates and the thiocyanates, have properties that are beneficial to health, and in particular anticarcinogenic properties. It is described in literature, for example, that isothiocyanates induce the activity of phase II enzymes, which are known to be involved in the detoxification and secretion of harmful compounds. It is also known that isothiocyanates can induce a programmed cell death in carcinomas. There is also evidence in literature of a correlation between elevated concentrations of indoles and thiocyanates in edible crops and a reduced risk of developing intestinal cancer, amongst other things. Attention has been focused for some time on the level and type of glucosinolates in *Brassica* plants due to their beneficial effect on health.

It is known, in particular, that two glucosinolates, and specifically their breakdown products, have pronounced anticarcinogenic properties. These glucosilonates are generally referred to as glucoiberine (3-methylsulphinylpropyl glucosinolate (3MSPG)) and glucoraphanin (4-methylsulphinylbutyl glucosinolate (4MSBG)).

In the literature available to date there are descriptions of attempts to raise the levels of glucosinlates, and in particular glucoiberine (3-methylsulphinylpropyl glucosinolate (3MSPG)) and glucoraphanin (4-methylsulphinylbutyl glucosinolate (4MSBG)).

U.S. Pat. No. 6,340,784, for example, describes the use of the elevated level of glucoiberine (3-methylsulphinylpropyl glucosinolate (3MSPG)) and glucoraphanin (4-methylsulphinylbutyl glucosinolate (4MSBG)) observed in 'wild', non-cultivated members of the *Brassica* varieties *Brassica villosa* and *B. drepanensis*. In this patent specification an attempt is made to introduce these properties by means of crossings into the cultivated, 'edible' *Brassica* varieties.

However, using these non-cultivated 'wild' *Brassica* varieties has the following significant drawbacks:

1) The use of non-cultivated 'wild' varieties can also lead to the introduction of undesirable glucosinolates into the edible crops ultimately produced. These may be, for example, glucosinolates that determine flavour, glucosinolates with a potent anti-nutritive property, toxic glucosinolates, etc.

2) In addition to the introduction of undesirable glucosinolates through the non-cultivated 'wild' *Brassica* varieties into the cultivated 'edible' *Brassica* varieties, it is possible that other properties that are not associated with glucosinolates and that are usually unknown, such as toxins, increased susceptibility to pathogens, reduced fertility, lower yield of edible parts, etc. will also be introduced.

3) Due to the relatively large genetic distance of *Brassica villosa* and *B. drepanensis* from the cultivars, their use calls for a very long (often covering several years or even decennia) and therefore extremely costly programme of (back)crossings, selections and analyses for producing once again a cultivatable *Brassica* crop.

4) The non-cultivated 'wild' varieties often have morphological features which consumers find unattractive, such as a hairy leaf, an unappealing colour, deviating and unrecognisable edible plant parts, etc.

With regard to the introduction of undesirable properties of non-cultivated 'wild' *Brassica* varieties into cultivated 'edible' varieties, it is interesting to note the practice of *Brassica napus* breeding where the lowering of certain harmful glucosinolates is a specific goal with respect to the production of cultivated crops.

This applies in particular to crops that are intended as animal feed. If large quantities of such harmful glucosinolates are absorbed by animals, harmful side effects occur, for example in the thyroid gland. An accumulation of glucosinolates in the thyroid gland interferes with the synthesis of the thyroid hormone. Additionally, thiocyanates inhibit the absorption of iodine compounds by the thyroid gland.

It is therefore an object of the present invention to produce cultivated 'edible' plants belonging to the Brassicaceae family with elevated levels of anticarcinogenic glucosinolates without the aforementioned drawbacks.

This object is achieved according to the invention with the *Brassica* plants which are produced by the method as described in claim 1. Claim 1 describes a method comprising:
a) providing a cultivated *Brassica oleracea* plant with elevated levels of anticarcinogenic glucosinolates in the edible parts of the *Brassica oleracea* plant;
b) the use of the *Brassica oleracea* plant provided under a) as the starting material for breeding *Brassica* varieties with elevated levels of anticarcinogenic glucosinolates,
wherein the anticarcinogenic glucosinolates comprise at least glucoiberin (3-methylsulphinylpropyl glucosinolate (3MSPG)) and/or glucoraphanin (4-methylsulphinylbutyl glucosinolate (4MSBG)), and wherein the concentration of 3MSPG per 100 gram of fresh weight of the edible part is greater than 100 micromol and the concentration of 4MSBG per 100 gram of fresh weight of the edible part is greater than 50 micromol.

It is known of plants belonging to the cultivated *Brassica oleracea* group that they are safe for consumption ('safe use') by humans and animals. This means in actual practice that it is generally assumed that these plants do not contain any compounds that are harmful for either humans or animals. Since this group of plants has been used for many centuries, it is also known that they do not have any harmful side effects even when consumed over a long period of time (many decennia). As a consequence, the chance of introducing undesirable properties, such as other harmful or unwanted glucosinolates or toxins, is reduced to a minimum, and probably even to zero.

Many vegetables belonging to the Brassicaceae family belong to the *Brassica oleracea* group. Since the *Brassica oleracea* plant produced according to the present invention has a relatively small genetic distance, if any distance at all, from the cultivated 'edible' *Brassica oleracea* plants obtained with elevated levels of anticarcinogenic glucosilonates, the latter plants can be obtained simply according to step b) whereby genetic material is exchanged by means of crosses.

Nor does the use of a plant belonging to the *Brassica oleracea* group produce any 'edible' plants or parts of plants which consumers consider to be unpalatable. There are many ways of providing a cultivated *Brassica oleracea* plant with elevated levels of anticarcinogenic glucosinolates in the edible parts.

For example, such a plant can be provided using molecular markers (hybridisation, restriction fragment length polymorphism (RFLP), PCR) and, in particular, by using molecular markers which are associated with genes which encode for enzymes that are involved in the synthesis of glucosinolates with an anticarcinogenic effect. Such enzymes are known to the average skilled artisan since the route for synthesis of glucosinolates has been revealed (see also figure 1).

A further possibility for the provision of a *Brassica oleracea* plant according to the present invention is an analysis of the expression level of genes, and in particular of those genes which encode for enzymes that are involved in the synthesis of glucosinolates. A reduced or elevated expression of a specific gene can indicate an enhanced concentration of glucosinolates with an anticarcinogenic effect. There are many methods available in this field, such as real time PCR, Northern Blot analysis, quantitative PCR, etc., all of which are part of the practical skills and knowledge of the average skilled artisan.

It is also possible to provide a *Brassica oleracea* plant according to a) by means of a biochemical determination of the concentration of anticarcinogenic glucosinolates. An example of such a biochemical determination is High Performance Liquid Chromatography, or HPLC for short. The concentration and the nature of the glucosinolates present in a specific *Brassica oleracea* plant can be determined simply with the aid of a chromatogram which gives a graphical presentation of the detected data of the HPLC. Other examples of biochemical methods are colouration of specific glucosinolates, immunological methods which reveal specific glucosinolates in tissue samples, mass spectrometry, NMR, infrared absorption analysis, etc.

A *Brassica oleracea* plant according to the present invention can also be provided using modern molecular biological methods. Such methods can be used, for example, for the in vivo influence of the expression of genes which encode for enzymes that are involved in the biosynthesis of glucosinolates. Examples of such methods are knock-out, knock-in, RNA silencing, anti-sense mRNA, etc.

Once a cultivated *Brassica oleracea* plant with elevated levels of anticarcinogenic glucosinolates has been provided, it can be used to introduce this property into plants belonging to the Brassicaceae family. Possible breeding methods include cross-fertilizations, anther culture, micro trace culture, protoplast fusion and genetic modification, which are commonly known within the field so that the average skilled artisan should have no difficulty choosing the most efficient method.

According to the present invention, the glucosinolates with an anticarcinogenic effect are the glucosinolates glucoiberine (3-methylsulphinylpropyl glucosinolate (3MSPG)) and/or glucoraphanin (4-methylsulphinylbutyl glucosinolate (4MSBG)). These glucosinolates have a very powerful anticarcinogenic effect. In order to increase the chance of producing a plant belonging to the Brassicaceae family with high levels of anticarcinogenic glucosinolates, the concentration of glucoiberin (3-methylsulphinylpropyl glucosinolate (3MSPG)) per 100 gram of fresh weight of the edible part should preferably be greater than 280 micromol, more preferably greater than 390 micromol and most preferably greater than 790 micromol. After all, there is always a chance that during the aforementioned step b), part of the high levels of anticarcinogenic glucosinolates that were originally produced will be lost.

This also applies with respect to glucoraphanin (methylsulphinylbutyl glucosinolate (4MSBG)). According to the present invention, the concentration of glucoraphanin (4-methylsulphinylbutyl glucosinolate (4MSBG)) per 100 gram of fresh weight of the edible part should preferably be greater than 120 micromol, and more preferably greater than 140 micromol.

The edible parts of the plant according to the invention include head cabbage (white, red and Savoy cabbage), stems (kohlrabi), cruciferous vegetables (broccoli, cauliflower and broccoli sprouts) and axillary buds (Brussels sprouts).

Several *Brassica oleracea* varieties are particularly suitable for use in the method according to the present invention. These are Savoy cabbage (*Brassica oleracea* convar. *capitata* var. *sabauda*), broccoli (*Brassica oleracea* convar. *botrytis* var. *cymosa*) and broccoli sprouts (*Brassica oleracea* convar. *botrytis* var. *asparagoides*). Of these varieties, broccoli sprouts are particularly suitable (*Brassica oleracea* convar. *botrytis* var. *asparagoides*).

Consumers prefer to eat fresh vegetables. Accordingly, broccoli sprouts enjoy favoured use since this variety exhibits very good cold hardiness as a consequence of which the variety can be grown throughout the year. This produces a constant supply (throughout the year) of fresh vegetables. Moreover, consumers prefer broccoli sprouts due to their familiar morphology.

The respective varieties of the races Wirosa (Savoy cabbage, annex 1), Belstar (broccoli, annex 2), Coronado (broccoli, annex 3) and Bordeaux (broccoli sprouts, annex 4) are specifically preferred. These races are characterised according to the corresponding descriptions of these varieties according to article 11, para. 2 of the Vegetable Seed Directive of the European Community (70/458/EEC).

The method according to the present invention is particularly suitable for the provision of plants belonging to the Brassiceae family, which plants are selected from the group comprising cauliflower or romanesco (*Brassica oleracea* convar. *botrytis* var. *botrytis*); broccoli (*Brassica oleracea* convar. *botrytis* var. *cymosa*); broccoli sprout (*Brassica oleracea* convar. *botrytis* var. *asparagoides*); Brussels sprouts (*Brassica oleracea* convar. *oleracea* var. *gemmifera*); white cabbage or oxheart cabbage (*Brassica oleracea* convar. *capitata* var. *alba*); red cabbage (*Brassica oleracea* convar. *capitata* var. *rubra*); Savoy cabbage (*Brassica oleracea* convar. *capitata* var. *sabauda*); kohlrabi (*Brassica oleracea* convar. *acephala* var. *gongyloides*); kale (*Brassica oleracea* convar. *acephala* var. *sabellica*); and Portuguese cabbage (*Brassica oleracea* var. *tronchuda* syn. *costata*).

The *Brassica* plants that are provided by the method according to the present invention have particularly desirable properties with respect to plants known from the art, and in particular having regard to their high levels of anticarcinogenic glucosinolates. The present invention therefore also relates to plants, seeds and parts of plants that can be obtained according to the method described above.

Due to their anticarcinogenic properties, the plants according to the present invention are particularly suitable for use in the preparation of a food product or pharmaceutical composition that can be used for prophylaxis and/or treatment of cancer. Examples of such use are food products in the form of salads, juice, bars, meals, snacks, etc. For pharmaceutical compositions the plants could be incorporated into tablets, injectible liquids, suppositories, capsules, suspensions, carriers, sustained release carriers, etc.

The present invention will be explained further below by reference to a number of examples which are in no way intended to restrict the invention in any respect and which are only meant to illustrate possible embodiments of the present invention.

EXAMPLES

Example 1

Starting Material

Plants of the various *Brassica oleracea* genotypes (see Table 1) all grew in the same field, hence in the same weather conditions and under an identical feeding regime. All plants received the same quantity of fertilizer (see Table 2). A total of 41 different *Brassica oleracea* genotypes were used.

TABLE 1

*Brassica oleracea* genotypes used

| | Sowing date | Planting date | Sample taken |
|---|---|---|---|
| White cabbage | | | |
| Almanac | 20 March | 13 May | 23 October |
| Krautman | 20 March | 13 May | 23 October |
| Mentor | 20 March | 13 May | 23 October |
| Mandy | 20 March | 13 May | 23 October |
| Lennox | 20 March | 13 May | 23 October |
| Danish 11-2 | 20 March | 14 May | 23 October |
| Red cabbage | | | |
| Integro | 1 May | 4 June | 2 October |
| Azzuro | 13 March | 13 May | 23 October |
| Huzaro | 14 March | 13 May | 23 October |
| Buscaro | 13 March | 13 May | 23 October |
| Pesaro | 13 March | 13 May | 23 October |
| Oxheart cabbage | | | |
| Bejo 2574 | 14 June | 15 July | 2 October |
| Bejo 2575 | 28 June | 29 July | 2 October |
| Capricorn | 14 June | 15 July | 2 October |
| Kohlrabi | | | |
| Kolibri | 12 July | 13 August | 8 October |
| Korist | 12 July | 13 August | 8 October |
| Broccoli | | | |
| Lucky | 21 June | 25 July | 2 October |
| Alborada | 21 June | 25 July | 2 October |
| Belstar | 21 June | 25 July | 2 October |
| Surveyor | 21 June | 25 July | 2 October |
| Coronado | 21 June | 25 July | 8 October |
| Bordeaux | 14 June | 16 July | 14 November |
| Cauliflower | | | |
| Jerez | 7 June | 9 July | 2 October |
| Cassius | 7 June | 9 July | 2 October |
| Encanto | 7 June | 9 July | 2 October |
| Skywalker | 31 May | 4 July | 2 October |
| Panther | 7 June | 8 July | 2 October |
| Romanesco | | | |
| Bejo 1955 | 7 June | 8 July | 2 October |
| Veronica | 7 June | 8 July | 2 October |
| Amfora | 7 June | 8 July | 2 October |
| Kale | | | |
| Ripbor | 17 May | 13 June | 23 October |
| Redbor | 17 May | 13 June | 23 October |
| Brussels sprouts | | | |
| Franklin | 1 March | 24 April | 8 October |
| Nautic | 1 March | 24 April | 23 October |
| Maximus | 1 March | 24 April | 23 October |
| Glenroy | 1 March | 24 April | 23 October |
| Doric | 1 March | 24 April | 23 October |
| Dominator | 1 March | 24 April | 14 November |
| Revenge | 1 March | 24 April | 14 November |
| Savoy cabbage | | | |
| Ovasa | 3 May | 5 June | 2 October |
| Wirosa | 3 May | 5 June | 2 October |

TABLE 2 fertilization data
On 21 Mar. 2002, a nitrogen sample was taken; the plot of
land where the *Brassica* plants were planted has its own
reserves of 70 kg of pure nitrogen.

| Element | Pure fertilizer | Fertilizer type | Concentration |
|---|---|---|---|
| Magnesium | 25 kg/ha | Kieserite | 100 kg/ha |
| Phosphate | 300 kg/ha | Triple Super Phosphate | 700 kg/ha |
| Potassium | 300 kg/ha | Patent-Kali | 1000 kg/ha |
| Nitrogen | 200 kg/ha | Lime Saltpetre | 500 kg/ha |

Example 2

Sampling

Five different plants or parts of a plant (leaf, sprouts, corolla) were harvested from each grown variety according to Table 1. Care was taken to avoid taking plants from the outer row in order to avoid peripheral effects.

Of the white cabbage varieties, 3 whole cabbages were harvested. Two facing segments, each being ⅛ of the cabbage, were taken from each cabbage. In the case of the broccoli varieties, 3 rosettes were cut from the centre and edge of the different plants. In the case of the sprouts, two facing quarters were taken as a sample from each plant.

The samples were then frozen using liquid nitrogen and pulverized. The resulting powder was stored at −20° C. for further processing and analysis.

Example 3

Extraction of Glucosinolates 5 grams of the powder obtained in example 2 was weighed and placed in 50 ml centrifuge tubes, which were subsequently heated in a water bath to 75° C. Then 12 ml of boiling methanol (100%) was added to the tubes and the suspension was mixed. 1.0 ml 3 mM of glucotropaeoline was then added immediately as an internal standard.

The sample was extracted in a water bath at 75° C. for not less than 20 minutes and regularly shaken. Thereafter the solid parts were pelleted by means of centrifugation (10 minutes, 5000×g) at room temperature and the supernatant was transferred to a clean centrifuge tube. The above extraction method was performed a further two times on the supernatant obtained, each time with 10 ml of boiling methanol (70%) solution. The extract obtained was stored at −20° C.

Example 4

Desulpherization of Glucosinolates 10 grams of DEAE Sephadex A-25 powder was measured out and to it was added 80 ml 2M of acetic acid. The suspension was then stored overnight at room temperature without being stirred. The volume of the suspension was then doubled by the addition of 2 M of acetic acid. A 2 ml syringe was sealed at the bottom with a wad of glass wool. The DEAE Sephadex suspension was carefully placed in this syringe until a column of approximately 1.5 ml had formed. The filled syringe was then transferred to a 10 ml test tube. Here the column was washed twice with 1 ml of water.

Approximately 2 ml of the supernatant was passed through the column obtained, according to example 3. The column was then washed twice with 1 ml 20 mM NaAc solution (pH 4.0). The column was transferred to a clean tube and 75:1 fresh sulphatase solution (25 mg Sulphatase type H-1 (Sigma s-9626)/ml bidest) was passed through the column. This enzyme was allowed to act on the column for one night at room temperature. The desulphated glucosinolates were then eluated using 3×0.5 ml bidest and the combined fractions were filtered through a 0.45:m filter (13 mm, Alltech).

Example 5

HPLC Analysis

For High Performance Liquid Chromatography (HPLC) analysis, use was made of equipment that permits gradient) elution. A UV detector set to a wavelength of 229 nm was connected to this equipment. An Alltech Optiguard® 1 mm reversed phase C18 reversed phase column was used as a pre-column. A Novapak C18 column was used as a separating column.

The eluents used for the column were composed as follows:
1) Eluent A: 0.05% tetramethylammoniumchloride (Merck).
2) Eluent B: 0.05% tetramethylammoniumchloride in $H_2O$/Acetonitril (80/20 v/v).

The injection volume was 20:1 and the total flow rate was kept at a constant 1.0 ml/min. The gradient profile at which the eluents passed through the column was as follows:

| Time (min) | Eluent A (%) | Eluent B (%) |
|---|---|---|
| 0 | 100 | 0 |
| 1 | 100 | 0 |
| 21 | 0 | 100 |
| 26 | 100 | 0 |
| 31 | 100 | 0 |

After the eluent had passed through the column, the $E_{229}$ was measured with the aid of a UV detector.

Example 6

Reference Samples Used

The following internal standards were used for internal reference purposes:
a) Glucotropaeolin (KLV, Denmark)
b) Sinigrin
c) Gluconasturtin
d) Sprout (Cyrus)
e) Rapeseed (Colza; BCR reference sample; No. 367R).

Example 7

Determination of Glucosinolate Levels

The level of glucosinolates (GLS) was determined with respect to the internal standard (IS) and is expressed in micromol/100 gram fresh weight. The relative response factor (RRF) with respect to glucotropaeolin of the measured substances was determined. These data are summarised in Table 3. The concentration of glucosinolates in each sample was then determined with a correction being made using the relative response factor found. The results are presented in Table 4.

TABLE 3

Relative response factors with respect to glucotropaeolin

| DESULPHOGLUCOSINOLATE | GLUCOTROPAEOLIN |
|---|---|
| glucoiberin | 1.126 |
| progoitrin | 1.147 |
| sinigrin | 1.053 |
| glucoalyssin | 1.13 |
| glucoraphanin | 1.126 |
| gluconapoleiferin | 1.00 |
| gluconapin | 1.168 |
| 4-hydroxyglucobrassicin | 0.295 |
| glucotropaeolin | — |
| glucobrassicin | 0.526 |
| glucosturtin | 1.00 |
| 4-methoxyglucobrassicin | 0.26 |
| neoglucobrassicin | 0.21 |

TABLE 4

Glucosinolate levels measured in tested *Brassica oleracea* genotypes. All values were measured in duplicate and expressed as micromol glucosinolates per 100 gram of fresh weight. In literature, the level of glucosinolates is often represented as micromol/gram of dry weight. The values measured and the values found in literature can be resolved into one another with the following conversion factor: cabbage has a dry material level of 7–15%; average 10%. Therefore, 100 gram of fresh weight corresponds (on average) to 10 gram of dry weight; accordingly, the values in the table must be divided by 10 in order to allow comparison with values in literature.

|  | Glucoiberin (3MSPG) | 3MSPG (%) | Glucoraphanin (4MSBG) | 4MSBG (%) | Other glucosinolates | Total glucosinolates |
|---|---|---|---|---|---|---|
| White cabbage | | | | | | |
| Almanac | 24.8 | 19.5% | 18.9 | 14.9% | 83.2 | 126.9 |
| Krautman | 67.7 | 39.2% | 1.9 | 1.1% | 102.9 | 172.5 |
| Mentor | 57.6 | 23.9% | 3.1 | 1.3% | 180.3 | 241.0 |
| Mandy | 100.0 | 42.9% | 28.3 | 12.1% | 105.0 | 233.3 |
| Lennox | 109.0 | 53.7% | 18.8 | 9.3% | 75.3 | 203.1 |
| Danish 11-2 | 60.7 | 31.5% | 3.8 | 2.0% | 127.9 | 192.4 |
| Red cabbage | | | | | | |
| Integro | 19.3 | 12.5% | 33.9 | 22.0% | 100.6 | 153.8 |
| Azurro | 13.8 | 14.8% | 7.2 | 7.7% | 72.0 | 93.0 |
| Huzaro | 13.1 | 7.7% | 61.8 | 36.4% | 94.9 | 169.8 |
| Buscaro | 36.4 | 15.1% | 38.9 | 16.2% | 165.0 | 240.3 |
| Pesaro | 31.2 | 14.6% | 43.5 | 20.4% | 138.9 | 213.6 |
| Oxheart cabbage | | | | | | |
| Bejo 2574 | 28.1 | 20.6% | 0.7 | 0.5% | 107.9 | 136.7 |
| Bejo 2575 | 72.0 | 43.6% | 9.2 | 5.6% | 84.1 | 165.3 |
| Capricorn | 31.2 | 36.8% | 5.0 | 5.9% | 48.6 | 84.8 |
| Kohlrabi | | | | | | |
| Kohlbri | 12.8 | 23.3% | 28.8% | 52.4% | 13.4 | 55.0 |
| Korist | 6.4 | 46.0% | 0.0 | 0.0% | 7.5 | 13.9 |
| Broccoli | | | | | | |
| Lucky | 20.6 | 21.3% | 35.8 | 37.0% | 40.4 | 96.8 |
| Alborada | 25.8 | 18.1% | 69.0 | 48.4% | 47.7 | 142.5 |
| Belstar | 26.1 | 11.2% | 129.7 | 55.5% | 77.9 | 233.7 |
| Surveyor | 26.1 | 18.8% | 57.8 | 41.7% | 54.7 | 138.6 |
| Coronado | 52.1 | 19.7% | 140.7 | 53.1% | 72.1 | 264.9 |
| Bordeaux | 395.6 | 74.2% | 26.7 | 5.0% | 110.9 | 533.2 |
| Cauliflower | | | | | | |
| Jerez | 16.8 | 36.5% | 2.8 | 6.1% | 26.4 | 46.0 |
| Cassius | 7.6 | 24.4% | 0.7 | 2.3% | 22.8 | 31.1 |
| Encanto | 10.5 | 25.2% | 0.0 | 0.0% | 31.1 | 41.6 |
| Skywalker | 10.2 | 31.4% | 0.0 | 0.0% | 22.3 | 32.5 |
| Panther | 34.2 | 57.8% | 7.9 | 13.3% | 17.1 | 59.2 |
| Romanesco | | | | | | |
| Bejo 1955 | 25.4 | 54.9% | 2.1 | 4.5% | 18.8 | 46.3 |
| Veronica | 15.9 | 32.9% | 12.4 | 25.6% | 20.1 | 48.4 |
| Amfora | 13 | 24.4% | 16.0 | 30.1% | 24.2 | 53.2 |
| Kale | | | | | | |
| Ripbor | 35 | 35.0% | 1.7 | 1.7% | 63.4 | 100.1 |
| Redbor | 23.4 | 14.6% | 0.0 | 0.0% | 136.4 | 159.8 |

TABLE 4-continued

Glucosinolate levels measured in tested *Brassica oleracea* genotypes.
All values were measured in duplicate and expressed as micromol glucosinolates per 100 gram of fresh weight. In literature, the level of glucosinolates is often represented as micromol/gram of dry weight. The values measured and the values found in literature can be resolved into one another with the following conversion factor: cabbage has a dry material level of 7–15%; average 10%. Therefore, 100 gram of fresh weight corresponds (on average) to 10 gram of dry weight; accordingly, the values in the table must be divided by 10 in order to allow comparison with values in literature.

|  | Glucoiberin (3MSPG) | 3MSPG (%) | Glucoraphanin (4MSBG) | 4MSBG (%) | Other glucosinolates | Total glucosinolates |
|---|---|---|---|---|---|---|
| Brussels sprouts | | | | | | |
| Franklin | 51.1 | 9.9% | 28.9 | 5.6% | 437.3 | 517.3 |
| Nautic | 37 | 11.5% | 41.8 | 13.0% | 243.2 | 322.0 |
| Maximus | 91.5 | 31.9% | 22.8 | 8.0% | 172.2 | 286.5 |
| Glenroy | 43.6 | 12.9% | 11.7 | 3.5% | 283.1 | 338.4 |
| Doric | 38.2 | 6.7% | 26.4 | 4.6% | 504.1 | 568.7 |
| Dominator | 83.3 | 13.3% | 9.2 | 1.5% | 532.4 | 624.9 |
| Revenge | 47.5 | 9.9% | 8.5 | 1.8% | 422.9 | 478.9 |
| Savoy cabbage | | | | | | |
| Ovasa | 55 | 54.3% | 0.7 | 0.7% | 45.8 | 101.5 |
| Wirosa | 284.8 | 59.7% | 7.8 | 1.6% | 183.8 | 476.4 |

Table 4 clearly shows high levels of glucoiberin (3-methylsulphinylpropyl glucosinolate (3MSPG)) in the Bordeaux (broccoli sprout), the Lennox (white cabbage), the Mandy (white cabbage) and the Wirosa (Savoy cabbage), the values being 395.6 micromol, 284.8 micromol, 109.0 micromol and 100.0 micromol, respectively. There are high levels of glucoraphanin (4-methylsulphinylbutyl glucosinolate (4MSBG)) in the varieties Coronado (broccoli), Belstar (broccoli), Alborada (broccoli) and Huzaro (red cabbage), the values being 140.7 micromol, 129.7 micromol, 69.0 micromol and 61.8 micromol, respectively.

Example 8

Data were gathered according to the same protocol at another location and another time. The results are presented in Table 5.

| Genotype | Progoitrin | Sinigrin | 4MSBG | 3MSPG | Gluconapin |
|---|---|---|---|---|---|
| Brussels sprouts | | | | | |
| Maximus | 27.3 | 67.6 | | 154.9 | 7.6 |
| Dominator | 65.3 | 153.3 | | 105.9 | 22.2 |
| Broccoli | | | | | |
| Surveyor | | | 47.1 | 18.1 | |
| Bordeaux | 2.7 | 72.1 | | 796.8 | |
| White cabbage | | | | | |
| Lennox | 10.5 | 73.4 | | 151.4 | 2.9 |

Annex I Wirosa
The Netherlands FORM II
Ministry of Agriculture, Nature Management and Fisheries -
Bezuidenhoutseweg 73, The Hague SUBJECT: Information according to article 11 par. 2 of the vegetable seed directive (70/458/EEC):
ADMISSION OF A NEW VARIETY

| | |
|---|---|
| 1. Species: | *Brassica oleraces L. convar. capitata (L.)* Alef. var. *sabauda* DC - Savoy cabbage |
| 2. Variety: | Wirosa |
| 3. Maintainer: | NL 8 - Bejo Zaden B. V. |
| 4. Date of admission: | |
| 5. Indication of the variety: | b |
| 6. Short description of the variety: | |

UPOV directive: TG/48/6

| UPOV no. | Characteristic | Class | Code | Remarks |
|---|---|---|---|---|
| | Seedling: anthocyanic colouring hypocotyl | present | 9 | |
| 1 | Plant: height | low to medium | 4 | |
| 2 | Plant: maximum diameter (incl. wrapper leaf) | — | — | |
| 3 | Plant: outer stem length | short to medium | 4 | |
| 4 | Plant: wrapper leaf attitude | half-raised | 5 | |
| 5 | Wrapper leaf: size | — | — | |

Annex I Wirosa
The Netherlands FORM II
Ministry of Agriculture, Nature Management and Fisheries - Bezuidenhoutseweg 73, The Hague

| | | | | |
|---|---|---|---|---|
| 6 | Wrapper leaf: blade shape | round | 3 | to reverse egg-shaped |
| 7 | Wrapper leaf: profile upper side of blade | cupping | 1 | weak |
| 8 | Wrapper leaf: knobbling | medium to pronounced | 6 | fine |
| 9 | Wrapper leaf: knob size | small | 3 | |
| 10 | Wrapper leaf: folding | — | — | |
| 11 | Wrapper leaf: colour (with waxy layer) | grey-green | 3 | |
| 12 | Wrapper leaf: colour intensity | dark | 7 | |
| 14 | Wrapper leaf: waxy layer | strong | 7 | |
| 15 | Wrapper leaf: leaf margin undulation | weak | 3 | |
| 16 | Wrapper leaf: leaf margin notching** | — | — | |
| 17 | Wrapper leaf: leaf margin crimping** | — | — | |
| | Cabbage: size | small to medium | 4 | |
| 18G | Cabbage: shape of longitudinal section | flattened circular | 2 | to circular |
| 19 | Cabbage: shape of base | — | — | |
| 20 | Cabbage: length | short | 3 | to medium-long |
| 21 | Cabbage: diameter | small to medium | 4 | |
| 22 | Cabbage: location of largest diameter | above centre | 1 | to centre |
| 23 | Cabbage: closure | half-closed | 2 | |
| 24 | Cabbage: bract knobbling | medium | 5 | |
| 25 | Cabbage: bract crimping | — | — | |
| 26 | Cabbage: colour of bract | green | 2 | |
| 27 | Cabbage: colour intensity of bract | light to medium | 4 | |
| 28 | Cabbage: bract anthocyanin content | weak | 3 | |
| 29 | Cabbage: inner colour | — | — | |
| 31 | Cabbage: firmness | firm | 7 | |
| 32 | Cabbage: internal structure | — | — | |
| 33 | Cabbage: inner stem length | long | 7 | |
| 34G | Harvest maturity | late | 7 | |
| 35 | Cracks in cabbage after harvest time | — | — | |
| 36 | *Fusarium oxysporum* f. sp. *conglutinans fysio* | — | — | |

| | |
|---|---|
| Distinctiveness: | Most similar to Hiversa, but with a shorter stem, a flatter leaf attitude and earlier formation of cabbage. |
| 7. Denomination in trials: | Wirosa |

Annex II Bordeaux
The Netherlands FORM II
Ministry of Agriculture, Nature Management and Fisheries - Bezuidenhoutseweg 73, The Hague SUBJECT: Information according to article 11 par. 2 of the vegetable seed directive (70/458/EEC):
ADMISSION OF A NEW VARIETY

| | |
|---|---|
| 1. Species: | *Brassica oleracea* L. convar. *botrytis* (L.) Alef. var. *cymosa* Duch - Broccoli |
| 2. Variety: | Belstar |
| 3. Maintainer: | NL 8 - H Bejo Zaden B. V. |
| 4. Date of admission: | 17-08-2000 |
| 5. Indication of the variety: | b |
| 6. Short description of the variety: | |

UPOV directive: TG/151/3

| UPOV no. | Characteristic | Class | Code | Remarks |
|---|---|---|---|---|
| 1 | Plant: number of stems | one | 1 | |
| 2 | Plant: height | medium | 5 | |
| 3 | Leaf: attitude | half-raised | 3 | |
| 4 | Leaf: length | medium | 5 | |
| 5 | Leaf: width | medium | 5 | |
| | Leaf: shape | elliptical | 5 | |
| 6 | Leaf: number of lobes | few | 3 | |
| 7 | Leaf blade: colour | grey-green | 2 | |
| 8 | Leaf blade: colour intensity | medium | 5 | |
| | Leaf: waxy layer | medium | 5 | |
| 9 | Leaf blade: anthocyanic colouring | absent | 1 | |
| 10 | Leaf blade: margin undulation | weak | 3 | |
| 11 | Leaf blade: margin indentation | very shallow to shallow | 2 | |
| 12 | Leaf blade: knobbling | weak | 3 | |

Annex II Bordeaux
The Netherlands FORM II
Ministry of Agriculture, Nature Management and Fisheries - Bezuidenhoutseweg 73, The Hague

|     | Characteristic | Class | Code | Remarks |
| --- | --- | --- | --- | --- |
|     | Leaf blade: knob size | medium to large | 6 | |
| 13  | Leafstalk: anthocyanic colouring | absent | 1 | |
| 14  | Leafstalk: length | medium | 5 | |
| 15  | Flower head: length of bifurcations at base | short | 3 | |
| 16  | Flower head: size | medium | 5 | |
| 17  | Flower head: shape | circular | 1 | to flattened circular |
| 18G | Flower head: colour | grey-green | 3 | |
| 19  | Flower head: colour intensity | medium | 5 | |
| 20  | Flower head: anthocyanic colouring | absent | 1 | |
| 21  | Flower head: intensity of anthocyanic colouring | — | — | |
| 22  | Flower head: scragginess | fine to medium | 4 | |
| 23  | Flower head: granularity | fine to medium | 4 | |
| 24  | Flower head: firmness | firm | 7 | |
| 25  | Flower head: bracteate | absent | 1 | |
| 26  | Plant: secondary flower heads | present | 9 | |
| 27  | Plant: presence of secondary flower heads | very weak to weak | 2 | |
| 28  | Flower: colour | yellow | 2 | |
| 29  | Flower: intensity of yellow colour | medium to dark | 6 | |
| 30  | Harvest maturity | late | 7 | to medium |
| 31  | Start of flowering | medium to late | 6 | |
|     | Type | annual | 1 | |

Distinctiveness: No comparable races. The race is characterised by a slightly lobed leaf, a medium grey-green flower head with fine to medium granularity and a rather late harvest maturity.
7. Denomination in trials: Bejo 1848

Annex III Belstar
The Netherlands FORM II
Ministry of Agriculture, Nature Management and Fisheries - Bezuidenhoutseweg 73, The Hague SUBJECT: Information according to article 11 par. 2 of the vegetable seed directive (70/458/EEC): ADMISSION OF A NEW VARIETY 1. Species: *Brassica oleracea* L. convar. *botrytis* (L.) Alef. var. *cymosa* Duch. - Broccoli
2. Variety: Coronado
3. Maintainer: NL 8 - H. Bejo Zaden B. V.
4. Date of admission: 30/04/1997
5. Indication of the variety: b
6. Short description of the variety:

UPOV directive: TG/151/3

| UPOV no. | Characteristic | Class | Code | Remarks |
| --- | --- | --- | --- | --- |
| 1  | Plant: number of stems | one | 1 | |
| 2  | Plant: height | medium | 5 | |
| 3  | Leaf: attitude | half-raised | 3 | |
| 4  | Leaf: length | medium | 5 | |
| 5  | Leaf: width | medium to broad | 6 | |
|    | Leaf: shape | elliptical to broad elliptical | 6 | |
| 6  | Leaf: number of lobes | medium | 5 | |
| 7  | Leaf blade: colour | grey-green | 2 | |
| 8  | Leaf blade: colour intensity | Medium to dark | 6 | |
|    | Leaf: waxy layer | strong | 7 | |
| 9  | Leaf blade: anthocyanic colouring | absent | 1 | |
| 10 | Leaf blade: margin undulation | very weak to weak | 2 | |
| 11 | Leaf blade: margin indentation | shallow | 3 | |
| 12 | Leaf blade: knobbling | very weak to weak | 2 | |
|    | Leaf blade: knob size | medium | 5 | |
| 13 | Leafstalk: anthocyanic colouring | absent | 1 | |
| 14 | Leafstalk: length | short to medium | 4 | |
| 15 | Flower head: length of bifurcations at base | short | 3 | |
| 16 | Flower head: size | medium | 5 | |
| 17 | Flower head: shape | circular | 1 | |

-continued

Annex III Belstar
The Netherlands FORM II
Ministry of Agriculture, Nature Management and Fisheries -
Bezuidenhoutseweg 73, The Hague

| | | | | |
|---|---|---|---|---|
| 18G | Flower head: colour | grey-green | 3 | |
| 19 | Flower head: colour intensity | medium to dark | 6 | |
| 20 | Flower head: anthocyanic colouring | absent | 1 | |
| 21 | Flower head: intensity of anthocyanic colouring | — | — | |
| 22 | Flower head: scragginess | medium | 5 | |
| 23 | Flower head: granularity | fine to medium | 4 | |
| 24 | Flower head: firmness | medium | 5 | |
| 25 | Flower head: bracteate | absent | 1 | |
| 26 | Plant: secondary flower heads | absent | 1 | |
| 27 | Plant: presence of secondary flower heads | — | — | |
| 28 | Flower: colour | yellow | 2 | |
| 29 | Flower: intensity of yellow colour | light to medium | 4 | |
| 30 | Harvest maturity | very late | 9 | to late |
| 31 | Start of flowering | — | — | |
| | *Fusarium oxysporum* f. sp. *conglutinans fysio* 1 | resistant | 9 | |

| | |
|---|---|
| Distinctiveness: | No comparable races. The race is characterised by a half-raised leaf with very slight knobbling and a pronounced waxy layer, a circular, grey-green, medium firm flower head and a very late to late harvest maturity. |
| 7. Denomination in trials: | Bejo 1744 |

Annex IV Coronado
The Netherlands FORM II
Ministry of Agriculture, Nature Management and Fisheries -
Bezuidenhoutseweg 73, The Hague SUBJECT: Information according to article 11 par. 2 of the vegetable seed directive (70/458/EEC): ADMISSION OF A NEW VARIETY

| | |
|---|---|
| 1. Species: | *Brassica oleracea* L. convar. *botrytis* (L.) Alef. var. *cymosa* Duch - Broccoli |
| 2. Variety: | Bordeaux |
| 3. Maintainer: | NL 8c - H. Bejo Zaden B. V./Elso |
| 4. Date of admission: | 17/08/2000 |
| 5. Indication of the variety: | b |
| 6. Short description of the variety: | |

UPOV directive: TG/151/3

| UPOV no. | Characteristic | Class | Code | Remarks |
|---|---|---|---|---|
| 1 | Plant: number of stems | one | 1 | |
| 2 | Plant: height | very high | 9 | |
| 3 | Leaf: attitude | raised to half-raised | 2 | |
| 4 | Leaf: length | medium | 5 | |
| 5 | Leaf: width | narrow | 3 | |
| | Leaf: shape | narrow elliptical | 3 | |
| 6 | Leaf: number of lobes | very many | 9 | |
| 7 | Leaf blade: colour | blue-green | 3 | |
| 8 | Leaf blade: colour intensity | very dark | 9 | |
| | Leaf: waxy layer | very strong | 9 | |
| 9 | Leaf blade: anthocyanic colouring | absent | 1 | |
| 10 | Leaf blade: margin undulation | medium | 5 | |
| 11 | Leaf blade: margin indentation | shallow | 3 | |
| 12 | Leaf blade: knobbling | very weak to weak | 2 | |
| | Leaf blade: knob size | very small to small | 2 | |
| 13 | Leafstalk: anthocyanic colouring | present | 9 | |
| 14 | Leafstalk: length | short | 3 | |
| 15 | Flower head: length of bifurcations at base | very long | 9 | |
| 16 | Flower head: size | very small | 1 | |
| 17 | Flower head: shape | — | — | |
| 18G | Flower head: colour | violet | 5 | |
| 19 | Flower head: colour intensity | medium | 5 | |
| 20 | Flower head: anthocyanic colouring | present | 9 | |
| 21 | Flower head: intensity of anthocyanic colouring | very strong | 9 | |

-continued

Annex IV Coronado
The Netherlands FORM II
Ministry of Agriculture, Nature Management and Fisheries -
Bezuidenhoutseweg 73, The Hague

| 22 | Flower head: scragginess | — | — |
| --- | --- | --- | --- |
| 23 | Flower head: granularity | — | — |
| 24 | Flower head: firmness | very floppy | 1 |
| 25 | Flower head: bracteate | — | — |
| 26 | Plant: secondary flower heads | present | 9 |
| 27 | Plant: presence of secondary flower heads | very strong | 9 |
| 28 | Flower: colour | yellow | 2 |
| 29 | Flower: intensity of yellow colour | — | — |
| 30 | Harvest maturity | very late | 9 |
| 31 | Start of flowering | very late | 9 |
|  | Type | annual | 1 |

Distinctiveness: No comparable races. The race is characterised by a very tall plant, a very dark blue-green, narrow leaf with very many lobes, and very small purple flower heads (type purple sprouting broccoli).

7. Denomination in trials: BE 1891

The invention claimed is:

1. A method for providing *Brassica* varieties with elevated levels of anticarcinogenic glucosinolates, comprising:
    a) crossing a cultivated *Brassica oleracea* plant with a second *Brassica oleracea* plant; and
    b) identifying a progeny *Brassica oleracea* plant that has at least 100 micromol gluboiberin (3-methylsulphinylpropyl glucosinolate (3MSPG)) per 100 gram of fresh weight of the edible part,
        wherein the cultivated *Brassica oleracea* plant is sprouting broccoli (*Brassica oleracea* convar. *botrytis* var. *asparagoides*) variety Bordeaux or savoy cabbage (*Brassica oleracea* convar. *capitata* var. *sabauda*) variety Wirosa,
        wherein, in the cultivated *Brassica oleracea* plant, the anticarcinogenic glucosinolates include at least 3MSPG and glucoraphanin (4-methylsulphinylbutyl glucosinolate (4MSBG)), and
        wherein, in the cultivated *Brassica oleracea* plant, the concentration of 3MSPG per 100 gram of fresh weight of the edible part is greater than 280 micromol.

2. The method according to claim 1, wherein the concentration of 3MSPG per 100 gram of fresh weight of the edible part is greater than 390 micromol.

3. The method according to claim 1, wherein the concentration of 3MSPG per 100 gram of fresh weight of the edible part is greater than 790 micromol.

4. The method according to claim 1, wherein the concentration of 4MSBG per 100 gram of fresh weight of the edible part is greater than 140 micromol.

5. The method according to claim 1, wherein the cultivated *Brassica oleracea* plant is sprouting broccoli (*Brassica oleracea* convar. *botrytis* var. *asparagoides*) variety Bordeaux.

6. The method according to claim 1, wherein the cultivated *Brassica oleracea* plant is Savoy cabbage (*Brassica oleracea* convar. *capitata* var. *sabauda*) variety Wirosa.

7. The method according to claim 1, wherein the second *Brassica oleracea* plant is selected from the group consisting of sprouting broccoli (*Brassica oleracea* convar. *botrytis* var. *asparagoides*) of variety Bordeaux; and Savoy cabbage (*Brassica oleracea* convar. *capitata* var. *sabauda*) of variety Wirosa.

8. A method for providing *Brassica* varieties with an elevated level of glucoiberin (3-methylsulphinylpropyl glucosinolate (3MSPG)), comprising:
    a) crossing a cultivated *Brassica oleracea* plant with a second *Brassica oleracea* plant, wherein the cultivated *Brassica oleracea* plant is sprouting broccoli (*Brassica oleracea* convar. *botrytis* var. *asparagoides*) variety Bordeaux or savoy cabbage (*Brassica oleracea* convar. *capitata* var. *sabauda*) variety Wirosa; and
    b) identifying a progeny *Brassica oleracea* plant that has at least 100 micromol 3MSPG per 100 gram of fresh weight of the edible part.

* * * * *